US012667489B2

(12) United States Patent
Dolzan

(10) Patent No.: US 12,667,489 B2
(45) Date of Patent: Jun. 30, 2026

(54) MODULAR LASER THERAPEUTIC DEVICE

(71) Applicant: Vita Dolzan, Litija (SI)

(72) Inventor: Vita Dolzan, Litija (SI)

( * ) Notice: Subject to any disclaimer, the term of this patent is extended or adjusted under 35 U.S.C. 154(b) by 728 days.

(21) Appl. No.: 17/930,851

(22) PCT Filed: Mar. 11, 2021

(86) PCT No.: PCT/EP2021/056263
§ 371 (c)(1),
(2) Date: Sep. 9, 2022

(87) PCT Pub. No.: WO2021/180891
PCT Pub. Date: Sep. 16, 2021

(65) Prior Publication Data
US 2024/0197533 A1    Jun. 20, 2024

(30) Foreign Application Priority Data

Mar. 11, 2020    (EP) .................................... 20162336

(51) Int. Cl.
A61F 9/008        (2006.01)
(52) U.S. Cl.
CPC ........ A61F 9/00823 (2013.01); A61F 9/0084 (2013.01); A61F 2009/00863 (2013.01); A61F 2009/00874 (2013.01); A61F 2009/00876 (2013.01); A61F 2009/00889 (2013.01); A61F 2009/00891 (2013.01)
(58) Field of Classification Search
None
See application file for complete search history.

(56) References Cited

U.S. PATENT DOCUMENTS

| 6,210,401 B1 * | 4/2001 | Lai ....................... B23K 26/032 |
| | | 606/4 |
| 9,883,971 B2 * | 2/2018 | Dolzan ................. A61F 9/0084 |
| 11,128,098 B2 * | 9/2021 | Schultz ............... H01S 3/08059 |
| 11,957,621 B2 * | 4/2024 | Herekar .............. A61F 9/00821 |
| 12,228,399 B2 * | 2/2025 | Hartmann .......... G01B 11/2441 |

(Continued)

FOREIGN PATENT DOCUMENTS

| EP | 0458681 A1 | 11/1991 |
| EP | 2914227 B1 | 10/2013 |

(Continued)

OTHER PUBLICATIONS

Japanese Office Action dated Dec. 11, 2024 for the Japanese Application No. 2022-554794.

(Continued)

*Primary Examiner* — Shirley X Jian
(74) *Attorney, Agent, or Firm* — Dinsmore & Shohl LLP

(57)        ABSTRACT

The invention relates to a modular Modular Laser Therapy Device (MLTD) to be used by ophthalmologists for eye surgery that integrates three most frequently used therapeutic devices into a single, compact unit enabling the treatment with capsulotomy, vitreolysis and iridotomy, with selective laser trabeculoplasty and with photocoagulation. While providing such modular laser device a method is provided for optomechanically coupling different ophthalmic modules into the single unit using two laser sources.

18 Claims, 6 Drawing Sheets

(56)                References Cited

U.S. PATENT DOCUMENTS

| | | | |
|---|---|---|---|
| 2005/0183273 A1* | 8/2005 | Amron ................. | G01C 15/004 |
| | | | 33/289 |
| 2015/0157506 A1 | 6/2015 | Feklistov et al. | |
| 2015/0297408 A1* | 10/2015 | Dolzan ............... | A61F 9/00781 |
| | | | 606/3 |
| 2015/0366713 A1* | 12/2015 | Shazly .................... | A61B 3/12 |
| | | | 606/5 |
| 2016/0183782 A1* | 6/2016 | Yu .......................... | A61B 90/20 |
| | | | 606/4 |
| 2018/0160898 A1* | 6/2018 | Yoo .......................... | A61B 3/10 |
| 2019/0282403 A1* | 9/2019 | Barrett ............... | A61F 9/00825 |
| 2019/0341736 A1* | 11/2019 | Schultz ................ | H01S 3/1115 |
| 2020/0046553 A1* | 2/2020 | Barrett .................... | A61F 9/008 |
| 2020/0054489 A1* | 2/2020 | Thyzel ............... | A61F 9/00802 |
| 2023/0329911 A1* | 10/2023 | Sacks .................. | A61F 9/00821 |
| 2024/0197533 A1* | 6/2024 | Dolzan ................. | A61F 9/0084 |

FOREIGN PATENT DOCUMENTS

| | | | |
|---|---|---|---|
| JP | 2007181634 A | 7/2007 | |
| JP | 2016193072 A | 11/2016 | |
| WO | 1999/58047 A1 | 11/1999 | |
| WO | 2004/027487 A1 | 4/2004 | |
| WO | 2007/043052 A2 | 4/2007 | |
| WO | 2019/060756 A1 | 3/2019 | |
| WO | 2019116286 A2 | 6/2019 | |

OTHER PUBLICATIONS

International Search Report and Written Opinion issued by the European Patent Office acting as International Searching Authority for International Patent Application No. PCT/EP2021/056263 dated May 19, 2021 (14 total pages).

\* cited by examiner

MODULAR LASER THERAPEUTIC DEVICE

CROSS REFERENCES TO RELATED APPLICATIONS

This application is a national-stage application under 35 U.S.C. § 371 of International Application No. PCT/EP2021/056263, filed Mar. 11, 2021, which International Application claims benefit of priority to European Patent Application No. 20162336.0, filed Mar. 11, 2020.

FIELD OF THE INVENTION

The invention is related to a modular Modular Laser Therapy Device (MLTD) to be used by ophthalmologists for eye surgery that integrates three most frequently used therapeutic devices into a single, compact unit enabling the treatment with capsulotomy, vitreolysis and iridotomy, with selective laser trabeculoplasty and with photocoagulation.

BACKGROUND OF THE INVENTION a) Introduction to Therapeutic Procedures and Ophthalmic Laser Treatment a1) Photodisruptor (PD) Procedures One of most frequent eye diseases is cataract which occurs as opacification of the lens inside the eye that leads to a change in refractive power and results in scattering of the incident light and reduced light intensity reaching the retina. Cataract is strongly related with biological ageing and around 75% of people over the age of 75 years suffer from lens opacities. Cataract can be efficiently treated with surgical intervention to replace the opaque lens with an artificial intraocular lens. It is estimated that approximately 20 million cataract surgeries are performed worldwide each year. However, within a period of 5 years after lens replacement opacities may occur in the posterior lens capsule in up to 30% of patients. Such posterior capsule opacification called secondary cataract and late-postoperative capsular bag distension syndrome are the most common postoperative complications of cataract surgery and affect the vision.

Secondary cataract is treated by laser posterior capsulotomy with a photodisruptor (PD) containing a Nd:YAG pulsed laser using nanosecond Nd:YAG laser pulses with wavelength 1064 nm and energies of 0.5 to 10 milliJoules with the excitation pulse focused just behind the intraocular lens and posterior capsule, typically to 100-200 micrometers. This high-intensity laser pulse induces an optical breakdown resulting in a micro explosion initiated by plasma formation. Plasma expansion is followed by different laser-induced phenomena, such as a shock wave and the cavitation bubble, which are responsible for posterior capsule disruption in a small area around the focal point. In order to clear the visual axis and improve patient's vision, a central opening in the opacified posterior capsule is performed by 30-50 pulses that are focused at different positions most commonly forming a cross. This creates an opening in the posterior surface of the lens capsule and normal vision is achieved through this opening.

Photodisruption with ns laser pulses is also emerging as method for precise and noninvasive microsurgery (fragmentation of tissue) inside the eye and has become the second most important therapeutic laser application in ophthalmology after photocoagulation. Nd:YAG laser can also be used for vitreolysis enabling safe and effective treatment in patients with symptomatic vitreous floaters in the posterior segment. Another application is iridotomy, a procedure for creating a small hole in the iris to treat and prevent acute angle closure glaucoma.

a2) Selective Laser Trabeculoplasty (SLT) Procedures

Glaucoma is a progressive neurodegenerative disease that threatens the sight of more than 50 million people worldwide, with the number of annual cases significantly on the rise and is the second most common cause of blindness in the developed countries. It is characterized by an irreversible loss of retinal ganglion cells and their axons that lead to a change in the structure of retinal nerve fiber layer and the optic nerve head. The most relevant risk factors for the development of glaucoma are age, race, family history and an increased intraocular pressure (IOP). Currently increased IOP is the only treatable risk factor associated with glaucoma. Besides drug-based therapy with eye drops microsurgical or laser-based interventions are also increasingly used.

Most frequently Selective Laser Trabeculoplasty (SLT) is used to target trabecular meshwork tissue. The mechanism underlying SLT is not completely elucidated. SLT procedure is using extremely short pulses from Nd:YAG laser that are frequency doubled to 532 nm and have duration of 1 to 5 nanoseconds and energy of 0.2 to 1.5 mJ to target 400 μm area within the trabecular meshwork. These specific treatment settings limit the heat-related damage and preserve the trabecular meshwork. Such laser pulses induce selective photothermolysis of the intracellular melanin granules in the trabecular meshwork cells, resulting in release of cytokines that trigger a targeted macrophage response. This leads to reduced resistance to fluid outflow in the meshwork, followed by lowering of the IOP in patients with open-angle glaucoma.

SLT is an improvement over a previously used technique referred to as argon trabeculoplasty (ALT). The method of ALT uses a thermal effect to coagulate the trabecular meshwork and thus enhance the flow of aqueous humor. Due to thermal effects the ALT method irreversibly damages the meshwork and can be applied only once or twice at the most. Surgery with SLT uses laser pulses shorter than 5 ns, in which thermal effects are negligible and can be repeated for an optional number of times.

Another laser microsurgical procedure that may be used for treatment of glaucoma is laser peripheral iridotomy during which laser induced PD is used to perforate the iris and increase the drainage of the fluid to lower the intraocular pressure.

a3) Photocoagulator (PC) Procedures

Laser-induced photocoagulation is the preferred standard treatment that can reduce or prevent severe visual loss in the wet form of age related macular degeneration, proliferative diabetic retinopathy, diabetic macular edema as well as other vitreo-retinal diseases.

Age related macular degeneration (AMD) is age related eye disease that is the major cause of blindness in the developed countries. Its first stage called age-related maculopathy (ARM) is characterized by changes of the pigment distribution and the formation of drusen in the retinal pigment epithelium. This stage progresses to the advanced stages called dry and wet AMD. Dry AMD accounts for 85% of AMD and is characterized by irreversible and progressive structural changes that lead to geographical atrophy and appearance of depigmented areas that grow in diameter. At present, there is no suitable therapy for AMD and dry ARM. In 25% of AMD patients, disease progresses to wet AMD form, characterized by formation of the new abnormal blood vessels in the choroid beneath the retina. These vessels are very fragile and leaky, leading to the appearance of the edema, retinal pigment epithelium detachment and/or bleeding that may dramatically reduce the quality of vision. Laser assisted photocoagulation (PC) has been widely used for treatment of these symptoms of wet AMD.

Diabetic retinopathy is a late complication of diabetes mellitus that is the most common cause of blindness in the working-age group in the developed countries. In its non-proliferative stage the increased permeability of the capillaries results in punctuate hemorrhages, development of microaneurysms and macular edema. In advanced stages, development of abnormal vessels, multiple bleedings, retinal detachment and/or microinfarctions appear in the retina and/or optic nerve head. If non-treated, 50% of patients may become blind within several years.

Laser-induced photocoagulation (PC) is the preferred standard treatment that can reduce or prevent severe visual loss in proliferative diabetic retinopathy, diabetic macular edema as well as other vitreo-retinal diseases.

Photocoagulation uses continuous laser power source to target and create thermal burns in small areas of the retina and the abnormal blood vessels beneath the macula. When energy from a frequency doubled Nd:YAG laser source at 532 nm is absorbed by the retinal pigment epithelium (RPE), it is converted into thermal energy.

Coagulation necrosis occurs with denaturation of cellular proteins as temperature rises above 65° C. The burns form scar tissue that seals the blood vessels, keeping them from leaking and thus slowing down the buildup of fluid under the retina that distorts the shape and position of the macula, the growth of scar tissue and the abnormal membrane under the retina, all of which damage the cells in the macula and lead to central vision loss.

Effective retinal photocoagulation requires an unobscured view of the retinal tissue for light to be absorbed by pigments in the retinal tissue. The degree of laser energy absorption in retinal layers and structures is highly dependent on the wavelength used and one of the major absorbing chromophores within the RPE cells is melanin. Melanin absorbs green, yellow, red and infrared wavelengths; xanthophyll in the macula absorbs blue with minimal yellow or red wavelength absorption, while hemoglobin absorbs blue, green and yellow with minimal red wavelength absorption. Although the current retinal lasers use wavelengths that are strongly absorbed by the melanin in RPE cells, the duration of the laser pulses which are currently used allows time for thermal diffusion from the RPE cells to adjacent structures and is particularly damaging to the neuro-retina resulting in permanent loss of visual function at the treatment site. Green 532 nm or yellow 577 nm laser is typically used to produce 50 to 500 μm spots spaced 0.5 to 1 burn widths from each other with 0.1 to 0.2 second exposure duration. Alternatively, laser delivery via indirect ophthalmoscopy offers better penetration through vitreous hemorrhage with better laser uptake.

b) Description of the Related Art (Prior-Art)

The main therapeutical ophthalmological devices for treatment of the above mentioned eye diseases are Selective Laser Trabeculoplasty (SLT) device for glaucoma treatment, Photodisruptor (PD) for secondary cataract treatment, vitreolysis and iridotomy, and Photocoagulator (PC) for retina treatment.

These devices are mostly used as separate ophthalmic devices, however some related prior-art solutions disclose combinations of two therapeutic ophthalmic modes in one integrated device. These laser systems are designed for use by ophthalmologists for performing SLT and PD procedure for the treatment of glaucoma and secondary cataract, respectively. However, none of the prior art discloses a therapeutic ophthalmic device that would enable integration of SLT and PD with PC within a single device.

EP0458681 (A1) (ALCON PHARMA) discloses an ophthalmic laser device using two laser modules and three optical paths, designed for use by ophthalmologists for performing SLT and PD procedure for the treatment of glaucoma and secondary cataract, respectively. Only one laser module is the therapeutic power source, namely a YAG laser emitting a 1064 nm pulse, while the other laser source produces an aiming beam. Integration of two ophthalmic treatment modules is achieved by a dichroic beam splitter, which allows for two optical paths from one laser source, one in transmission and one in reflection. So this solution does not allow for integration of additional optical paths needed to integrate additional therapeutic or diagnostic modules. This solution does not enable the addition of PC mode. Another problem of this prior-art is that it uses a plane-parallel plate as a substrate for the dichroic beam splitter in convergent rays. Such solution creates a large amount of aberrations and cannot satisfy high-quality imaging requirements. Therefore, it would be very difficult to implement this successfully in practice. Another problem not addressed in this prior-art is that collimating the frequency doubled wavelength of 532 nm in a small solid multimode optical fiber may damage the solid core of the fiber. Currently known new photonic hollow fibers having much higher damage threshold, didn't existent at the time of this prior-art. Hence, it is noted that the proposed laser system of this prior-art could never have been functional at the time of invention.

WO99/58047 (A1) (FRANS J VAN DE VELDE) discloses a combination of confocal scanning laser ophthalmoscope and external laser sources for microphotocoagulation of the retina or the measurement of wavefront aberrations of the eye optics. In the prior-art, an optomechanical linkage device with beam splitter allows independent positioning of the pivot point of the lasers of a scanning laser ophthalmoscope and the pivot point of non-scanning external laser beams. Again, the optical configuration with a plane-parallel plate, which is used as substrate for the beam splitter positioned in convergent rays, will create a large amount of aberrations, so it cannot satisfy high-quality imaging requirements.

WO 2004/027487/US2015157506 (A1) (Ellex) discloses an ophthalmic laser system generating pulses at first wavelength suitable for performing SLT and selectively generating pulses at second wavelength suitable for performing PD procedures. The laser system is able to select between directing the first beam or the second beam to the eye of a patient. An Nd:YAG laser source with a Q Switch generates a short pulse with a pulse length shorter than 5 ns at a wavelength of 1064 nm and the second beam is frequency doubled to 532 nm in a KTP doubling crystal. Integration of two ophthalmic treatment modules, using first beam for PD mode and second beam for SLT mode is achieved by polarization beam splitter. To set the energy in the photodisruptor mode a polarizer linearly attenuates pulse energy by rotation between 0.3 and 10 mJ. By rotating the polarizer in such a way, that a laser beam deflects from the polarizer in the optical path to another axis intended to generate a frequency doubled pulse for selective laser trabeculoplasty. Rotation of polarisation and a different deflection on the polarizer make this solution operational in two different optical paths, in the first path in the PD mode and in the second path in the SLT mode. In this solution, the basic laser beam is redirected by a deflection on the polarizer to another optical axis, where frequency doubling of the laser beam is performed. In this way the second optical path is used for the operation in the SLT mode. This solution allows for two optical paths from one laser source, one in transmission and one in reflection. So this solution does not allow for integration of additional optical paths for additional therapeutic module. Therefore this solution does not enable the addition of PC mode.

WO2007043052 (A2) (Lumenis) discloses a dual-path ophthalmic laser system designed for use by ophthalmologists for performing SLT and PD procedure for the treatment of glaucoma and secondary cataract, respectively. Integration of two ophthalmic treatment modules is achieved by dichroic beam splitter, which allows for two optical paths from one laser source, one in transmission and one in reflection. So this solution does not allow for integration of additional optical paths needed to integrate additional therapeutic or diagnostic modules. This solution does not enable the addition of PC mode.

Combined ophthalmic laser device U.S. Pat. No. 9,883,971 (B2), EP2914227 (B1) (Optotek) discloses a single path ophthalmic laser system designed for use by ophthalmologists for performing PD and SLT, at a laser wavelength of 1064 nm and at a frequency doubled wavelength 532 nm, respectively. The object of the invention is a laser device for eye surgery used by ophthalmologists for the treatment with capsulotomy and iridotomy, and a device for selective laser trabeculoplasty. The essence of the ophthalmic laser combined device of the invention lies in that it has one single laser with one optical path for both wavelengths; the basic wavelength of 1064 nm and the frequency doubled wavelength of 532 nm. Switching between both wavelengths is carried out by a polarization orientation switch. Frequency doubling is inactive at the wavelength of 1064 nm and it is active for the wavelength of 532 nm. At the wavelength of 532 nm additional optical elements for attenuating and collimating the laser pulse are switched on. This solution does not enable the addition of PC mode.

Aim of the Invention

The object of invention is to provide a modular Modular Laser Therapy Device (MLTD) to be used by ophthalmologists for eye surgery that integrates three most frequently used therapeutic devices into a single, compact unit enabling the treatment with capsulotomy, vitreolysis and iridotomy, with selective laser trabeculoplasty and with photocoagulation.

SUMMARY

The present invention provides an Modular Laser Therapy Device to be used by ophthalmologists for eye surgery that integrates three most frequently used therapeutic devices into a single, compact unit for treatment with photodisruptor mode (PD) for treatment with capsulotomy, vitreolysis and iridotomy, with selective laser trabeculoplasty (SLT) mode for glaucoma treatment and with photocoagulation (PC) mode for coagulation therapeutic procedures on retina.

The innovative approach proposed allows that one single device enabling different therapeutic modes can be used for treatment of a large number of eye diseases that are the most common causes of blindness in the world and have a huge impact on healthcare, society and economy: cataract is the major cause of blindness, accounting for 50% of all cases worldwide, followed by glaucoma (8%) and age-related macular degeneration (5%) (WHO (2012): Global data on visual impairments 2010).

With the present invention enabling Modular Laser Therapy Device (MLTD) a solution is provided for optomechanically coupling different ophthalmic modules into one single Modular Laser Therapy Device that uses two laser sources, the first laser source emitting pulses with first wavelength 1064 nm for treatment with capsulotomy, vitreolysis and iridotomy in Photodisruptor (PD) mode; the pulses from this first laser source can be frequency doubled by Selective Laser Trabeculoplasty (SLT) module to wavelength 532 nm for treatment with selective laser trabeculoplasty in SLT mode, and the second laser source emitting a continuous wave at second wavelength 532 nm for treatment with photocoagulation in Photocoagulator (PC) mode. Photodisruptor (PD) mode is enabled by integrating for example a Nd-Yag pulsed laser as first laser source, with energy meter/aiming beam module, the PD module and the exit objective module into one optical path. SLT mode is enabled by optomechanically coupling the first laser source with SLT module, energy meter/aiming beam module, scanning module and exit objective module. PC mode is enabled by optomechanically coupling the 532 nm continuous wave laser module with PC module, scanner module and exit objective module. All three devices are integrated into one single Modular Laser Therapy Device MLTD with the same exit objective lens for image and waist formation in the eye of the patient. In the SLT and PC mode, scanning in the image plane is enabled by the scanning module incorporating a pair of Risley prisms or alternatively a scanning mirror.

Switching between the three different modes of MLTD (PD, SLT and PC) is achieved by electromechanical, electronic and microprocessor control.

| | | | | | |
|---|---|---|---|---|---|
| 10 | first (PD/SLT) laser module | 40 | SLT module | 63 | correction prism |
| 11 | Nd-Yag pulsed laser | 41 | KTP crystal | 64 | first Risley prism |
| 12 | variable attenuator | 42A | Pass filter | 65 | second Risley prism |
| 13 | optical path first laser | 42B | SLT attenuator | 70 | exit objective lens module |
| 20 | energy meter/aiming beam module | 43 | fold mirror 1 | 71 | patient eye |
| | | 44 | fold mirror 2 | 72 | PD focal plane of 75 |
| 21 | beam splitter mirror | 45 | beam shaping lens | 72A | SLT focal plane of 75 |
| 22 | energy meter | 46 | beam shaping lens | 72B | PC focal plane of 75 |
| 23 | safety shutter | 50 | PC module | 73A | SLT add-on lens |
| 24 | beam combiner | 15 | second (PC) laser module | 73B | PC add-on lens |
| 25 | polarizing beam splitter/ combiner | 16 | optical fiber | 74 | PD beam path |
| | | 54 | PC zoom optics module | 74A | SLT beam path |
| 26 | aiming beam PD | 55 | beam shaping lens | 74B | PC beam path |

-continued

| 26A | aperture double PD | 56 | beam shaping lens | 75 | exit objective lens |
|-----|--------------------|----|-------------------|----|---------------------|
| 27 | aiming beam SLT | 57 | mirror | 77 | dichroic mirror |
| 30 | PD module | 60 | Scanner module | 78 | binocular |
| 31 | beam shaping lens | 61 | movable mirror | 79 | examiner's eye |
| 32 | beam shaping lens | 61A | switched off mirror | 80 | SLT/PC double platform |
| | | 62 | mirror | 80A | PD/SLT/PC single platform |

According to an aspect, the invention provides an ophthalmic laser system comprising: a first laser module (10) producing a beam (e.g. pulse) at a first wavelength; a second laser module (15) producing a beam at a second wavelength; a first beam path (74) incorporating beam shaping optics (31, 32) and an exit objective module (70) for directing the beam at said first wavelength to an eye of a patient (71); a second beam path (74A) incorporating a frequency modifying (e.g. frequency doubling) component (41) that converts the beam at the first wavelength to a beam at a third wavelength, beam shaping optics (45, 46) and said exit objective module (70) for directing the beam at said third wavelength to the eye of the patient (71); and a third beam path (74B) incorporating beam shaping optics (55, 56) and said exit objective module (70) for directing the beam at said second wavelength to the eye of the patient (71). A beam path is realized by a beam path arrangement comprising components and modules. According to an embodiment, such components and/or modules are movably mounted or mounted onto a platform being movable, so that the components and/or modules are switched in or out of the beam path using linear or rotational movement of the components, modules and/or platforms.

According to an aspect, the invention provides an ophthalmic laser system comprising laser modules, therapeutic optical modules and other electro-optical and/or optical modules and components that are movably mounted, or part of all components and modules are mounted onto a platform being movable so that the linear or rotational movement of the components, modules and/or a platform enable that laser pulses or beams from the laser modules are aligned with the desired therapeutic module and other said modules and with the exit objective module for image and waist formation in the eye of the patient.

According to an embodiment, with the laser modules comprising laser sources, three respective beam paths are realized by optoelectrical, optical and optomechanical means and by linear or rotational electromechanical movement of the components, modules and/or a platform:

a first beam path by aligning first laser module producing a pulse at a first wavelength, with PD beam shaping optics and an exit objective module for directing the pulse at the first wavelength to an eye of a patient for treatment with PD mode for capsulotomy, vitreolysis and iridotomy;

a second beam path by aligning first laser module producing a pulse at a first wavelength with a frequency modifying (e.g. frequency doubling) component that converts the pulse at the first wavelength to a pulse at a third wavelength, with SLT beam shaping optics, scanning module and the exit objective module for directing the pulse at the third wavelength to the eye of the patient for treatment with SLT mode for glaucoma treatment; and a third beam path aligning a second laser module producing a beam at a second wavelength with PC beam shaping optics, scanning module and the exit objective module for directing the beam at the second wavelength to the eye of the patient for treatment with PC mode for coagulation therapeutic procedures on retina.

Switching between or amongst the three different therapeutic modes (PD, SLT and PC) can be achieved by means of electromechanical, optomechanical, electronic and microprocessor control.

According to an embodiment, the core therapeutic modules can be fixed or movably mounted onto two platforms, so that PD module is mounted on fixed platform and SLT and PC modules are mounted on movable platform. The switching between the three different therapeutic modes (PD, SLT and PC) can be achieved by linear or rotational movements of the movable platform comprising of SLT module, PC module and scanning module, into the optical path of the fixed platform to disable the PD mode and to enable the coupling of the desired therapeutic module being either SLT module or PC module with the respective laser source being either first laser module or second laser module and with the exit objective module for image and waist formation in the eye of the patient.

Alternatively, the three core therapeutic modules, i.e. PD module, SLT module and PC module can be mounted onto a single platform being movable and the switching between the three different therapeutic modes (PD, SLT and PC) can be achieved by linear or rotational movements of components and/or modules onto such single platform to enable the coupling of the respective laser source with the desired therapeutic module and with the exit objective module for image and waist formation in the eye of the patient.

According to an embodiment, the ophthalmic laser modules are a first laser module comprising a laser source producing a pulse at a first wavelength of 1064 nm for treatment in PD mode; the pulses from this laser source can be frequency doubled to a third wavelength of 532 nm by means of SLT module for treatment in SLT mode; and a second laser module comprising a laser source producing a continuous wave beam at a second wavelength in the range from 440 nm to 650 nm for treatment in PC mode.

The first laser module comprises for example a pulsed Nd-YAG laser at first wavelength being nominally 1064 nm, which is (suitable) for secondary cataract treatment, whereas the first wavelength frequency doubled to third wavelength being nominally 532 nm is (suitable) for glaucoma treatment.

The second laser module comprises for example a continuous wave laser at wavelength being nominally 532 nm or a CW laser diode with third wavelengths from 440 to 680 nm, which is (suitable) for treatment with photocoagulation. The wavelength range may refer to the aiming beam generating laser diode.

According to an embodiment, the ophthalmic laser system comprises a first beam path incorporating an exit objective module for directing the pulse from the first laser module at first wavelength to the eye of the patient;

a second beam path incorporating a frequency modifying (e.g. frequency doubling) component that converts the pulse from the first laser module at first wavelength to a pulse at third wavelength, and the exit objective module for directing the pulse at third wavelength to the eye of the patient; and a third beam path incorporating the exit objective module for directing the beam from the second laser module at second wavelength to the eye of the patient.

First beam path may further incorporate PD beam shaping optics, and/or second beam path may further incorporate SLT beam shaping optics, and/or third beam path may further incorporate PC beam shaping optics.

Beam deflecting means may be incorporated into second beam path for deflecting the pulse at third wavelength towards SLT beam shaping optics in that second beam path.

First and/or second beam path may further incorporate a safety/aiming beam module for blocking off the beam path whenever such safety/aiming beam module detects an unsafe condition.

First and/or second beam path may further incorporate a safety/aiming beam module with two distinct aiming beam generators: aiming beam PD emitter with double aperture and aiming beam SLT emitter, as well as respective optics including beam splitters/combiners that enable collinear projection of the PD or SLT aiming beam with the therapeutic laser pulse in first and/or second beam path.

According to an embodiment, internal power meter and safety shutter are integrated within CW PC laser module, for blocking off third beam path whenever such internal power meter detects an unsafe condition.

According to an embodiment, aiming beam PC emitter, beam combiner and fiber collimating lens that collimates the PC beam and the aiming beam to optical fiber are integrated within CW PC laser module.

With the present invention, per therapeutic optical path, and thus per therapeutic wavelength, a respective aiming beam (at visual wavelength) is projected collinearly into the therapeutic optical path.

Second and/or third beam path may further incorporate a scanning module possibly being movable and comprising of a plurality of prisms amongst which for example Risley prisms, and/or comprising of one or more mirrors to enable scanning along x and y axis in the image plane in the patient's eye.

According to an embodiment, the first laser module is optomechanically aligned with the first or second beam path by linear or rotational movement of the movable optical modules and/or platforms and the second laser module is provided with a fiber coupling for selectively operating or enabling the third beam path. It is noted that with operating or operation here—and in general in the text, in accordance with the invention—of the laser (beam path) is meant the use or functionality thereof, and thus refers to how the laser (beam path) is used, enabled or manipulated in practice. In other words, operating or operation doesn't refer to e.g. surgery although the use of the laser (beam path) results in a medical treatment or therapeutics.

In an aspect of the invention, a method is provided for operating, i.e. using the ophthalmic laser system as referred to above, wherein either at least one of the ophthalmic modules is movably mounted, or part of all components and/or modules of the therapeutic beam paths is mounted onto a platform being movable.

Selectively switching between first, second or third beam path may be enabled by means of adaptable electromechanical and optomechanical coupling for at least part of all components and/or modules and/or platforms, and electromechanical, electronic and/or microprocessor control.

In an aspect of the invention, a method is provided for operating the ophthalmic laser system as referred to above, comprising the steps of selectively switching between the three different therapeutic modes (PD, SLT and PC) by linear or rotational movements of the modules and/or platforms to enable the coupling of the first or the second laser module with the desired therapeutic module and potentially a scanning module with the exit objective module for image and waist formation in the eye of the patient. The three different therapeutic modes are defined as (i) a photodisruptor (PD) mode wherein first beam path is operable using first laser module at first wavelength and aligned with PD module; (ii) a selective laser trabeculoplasty (SLT) mode wherein second beam path is operable using first laser module at third wavelength and aligned with SLT module and scanning module; and (iii) a photocoagulator (PC) mode wherein third beam path is operable using second laser module at second wavelength and aligned with PC module and scanning module. Switching between or amongst the three different modes (PD, SLT and PC) can be achieved by electromechanical, optomechanical, electronic and microprocessor control.

A major difference with the prior-art is that the present invention uses each of the three different optical paths for a separate therapeutic mode of action, targeting a different part of the eye: the lens capsule and the trabecular meshwork in the anterior eye segments and the retina in the posterior eye segment, respectively.

According to an embodiment, the ophthalmic laser system comprises components and modules for operating said first beam path (74) that are mounted on a first platform including said first laser module (10), and comprises components and modules for operating said second beam path (74A) that are mounted on a second platform, wherein at least one of said platforms is movably mounted for selectively operating for and amongst said first or second beam path (74, 74A). The ophthalmic laser system may further comprise components and modules for operating said third beam path (74B) that may be provided also onto said first or second platform. Said second laser module (15) may be provided with a fiber coupling for selectively operating said third beam path (74B). At least one of said components or modules may be movably mounted or may be mounted onto a platform being movable for selectively operating for and amongst said first or second or third beam path (74, 74A, 74B). Switching between and/or selecting amongst the different laser sources and optical paths is enabled by specific positioning of the movable modules or their components and/or movable platforms, at the same time preventing that undesired light from one of the other laser sources not being in use cannot reach the eye.

For an MD or physician, the advantage of the present invention is to have a single compact unit that enables three different therapeutic procedures, while saving costs and space requirement.

For an ophthalmic (laser) device or system manufacturer, the advantage may be to have simpler and more cost-effective production with less optical elements.

BRIEF DESCRIPTION OF THE DRAWINGS

The Modular Laser Therapy Device of the invention will be described in more detail in the continuation with reference to the following figures in which.

DETAILED DESCRIPTION OF THE INVENTION

Figure 1:
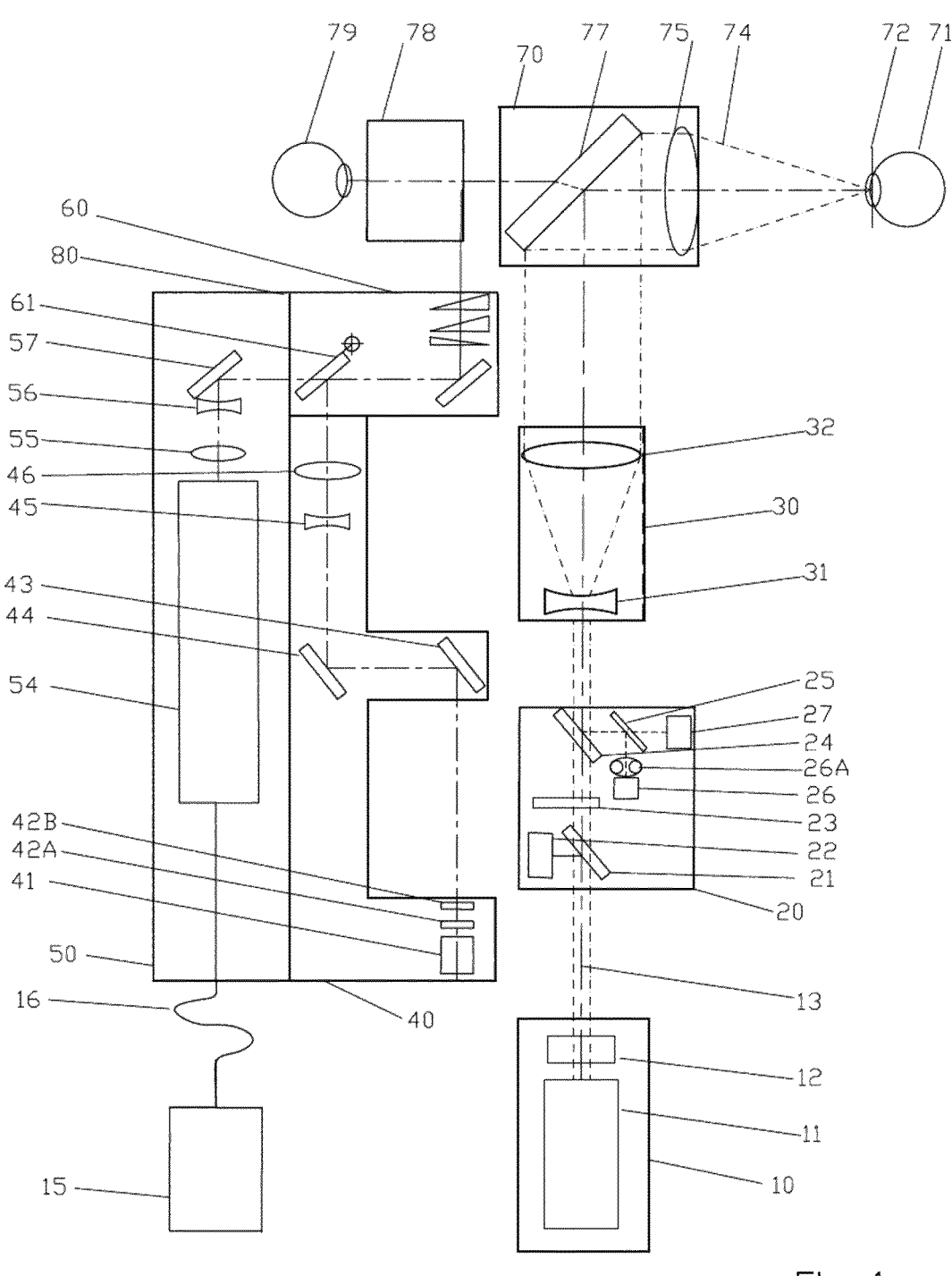
FIG. 1 shows an embodiment of a block diagram of the MLTD consisting of two platforms in a Photodisruptor (PD) mode, in accordance with the invention.

A problem that has remained unsolved in the art is a combined single Modular Laser Therapy Device for treatment with all the above mentioned procedures where operation of the Modular Laser Therapy Device (MLTD) would be enabled in all three modes, i.e. in PD mode, in SLT mode and in PC mode, by optomechanically switching different movable optical modules in and out of the optical paths.

The present invention brings solutions that enable integration of three therapeutic ophthalmic devices into a single modular Modular Laser Therapy Device (MLTD) that can be used for treatment of a large number of eye diseases as stated above.

These solutions allow combining optical paths of the laser module 10 or 15 with the optical paths of core optical modules integrated onto one or two platforms and enabling the desired mode of operation, these core therapeutic modules being PD module 30 for PD mode, SLT module 40 for SLT mode and PC module 50 for PC mode of action, with the optical path of the same exit objective module 70 for image and waist formation in the eye of the patient 71.

Switching between the three different therapeutic modes of MLTD (PD, SLT and PC) is achieved by linear or rotational movements of the platforms to enable the coupling of the first or the second therapeutic laser source with the desired therapeutic module and with the same exit objective module 70 for image and waist formation in the eye of the patient 71. Switching between the three different therapeutic modes of MLTD (PD, SLT or PC) is enabled by electromechanical, electronic and microprocessor control.

The combined Modular Laser Therapy Device (MLTD) of the invention uses two laser source modules, first laser module 10 containing pulsed laser source with basic wavelength of 1064 nm for PD mode; the pulses from this source can be frequency doubled to wavelength 532 nm for SLT mode, while the second (PC) laser module 15 emits a continuous wave in the range from 440 nm to 650 nm, nominally at 532 nm for treatment with PC mode.

MLTD uses three core optical modules for achieving the desired mode of operation, these core modules being PD module 30 for PD mode, SLT module 40 for SLT mode and PC module 50 for PC mode of action. The laser beam from the laser source module passes through the collinearly positioned core optical therapeutic module, being either PD module 30 for PD mode, SLT module 40 for SLT mode or PC module 50 for PC mode of action. PD, SLT and PC optical modules 30, 40 and 50, respectively can be integrated on two platforms or on one single platform, thus optimizing the number of optical components needed.

Respective energy meter/aiming beam modules 20 are being incorporated as core optical modules or within laser module 15.

In the SLT and PC mode, scanning module 60 enables scanning in the image plane by using a fixed correction prism 63 and a pair of Risley prisms 64, 65. The correction prism 63 enables shifting the beam out of the singularity zone of the Risley prisms. Alternatively, a scanning mirror 62 can be used.

Figure 2:
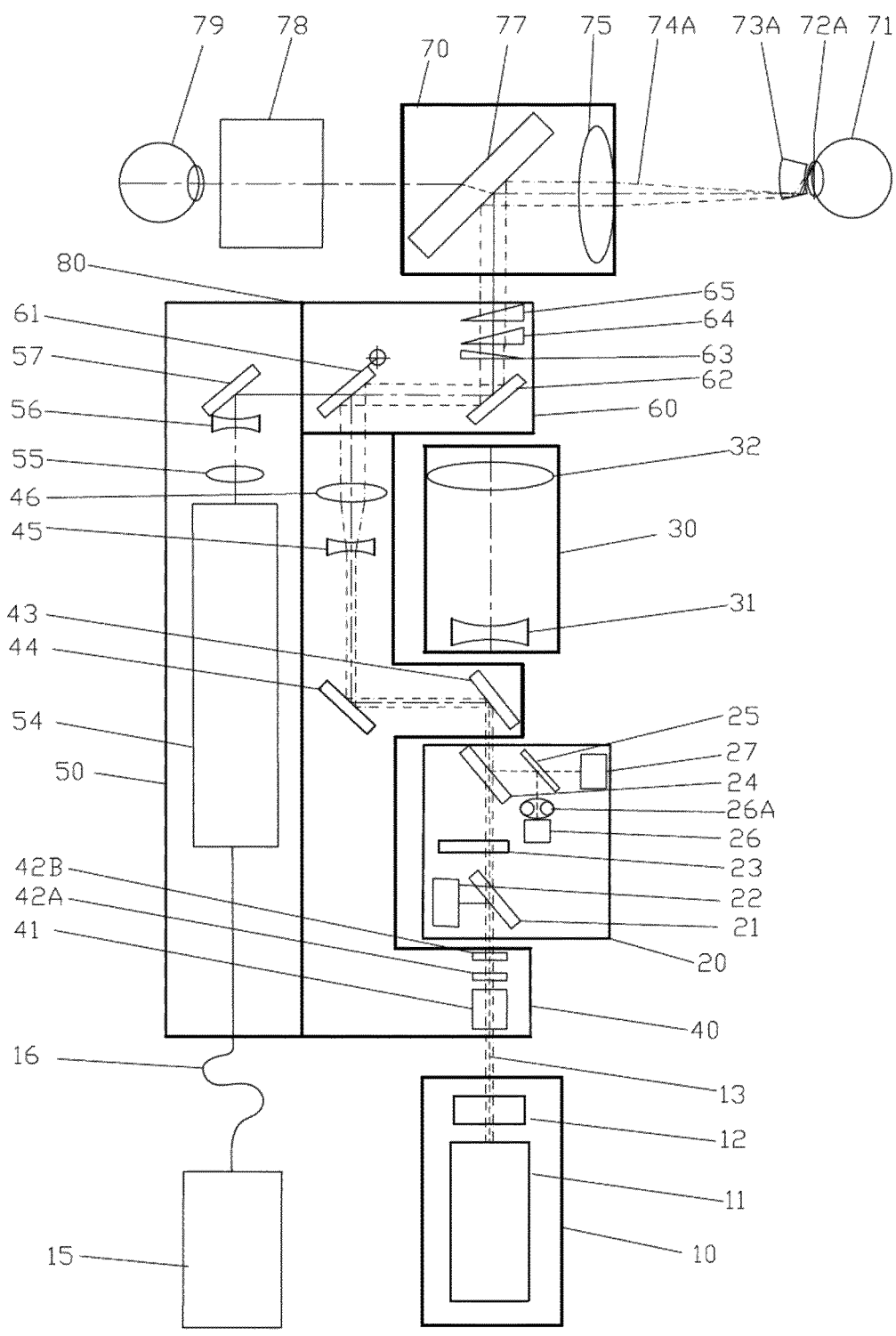
FIG. 2 shows an embodiment of a block diagram of the MLTD consisting of two platforms in a Selective Laser Trabeculoplasty (SLT) mode, in accordance with the invention.

The integration of the three therapeutic ophthalmic devices into a single modular Modular Laser Therapy Device may be achieved in two different ways:

1) Optical Solution with Two Platforms (See FIG. 1, FIG. 2. And FIG. 3 for Details)

PD module 30 is on a separate (e.g. fixed) platform, while SLT and PC modules are integrated onto one (e.g. movable) SLT/PC platform. Switching between PD and SLT or PC mode is carried out by means of mechanically moving SLT/PC platform 80 composed of SLT module 40, PC module 50 and scanner module 60, into the optical path 13 of the platform with the PD module 30.

PD mode (FIG. 1) is enabled by integrating the Nd-Yag pulsed laser module 10, with energy meter/aiming beam module 20, the PD module 30 and the exit objective module 70 into one optical path i.e. first beam path 74. When mechanically movable SLT/PC platform 80 composed of SLT module 40, PC module 50 and scanner module 60, is moved out of the optical path 13 of laser pulse of pulsed Nd:YAG laser source 10 at first wavelength 1064 nm, than device is working in PD mode.

SLT mode (FIG. 2) is enabled when mechanically movable SLT/PC platform 80 composed of SLT module 40, PC module 50 and scanner module 60 is moved into the optical path 13 of the PD module 30 using linear or rotational movement thus enabling the coupling of the exit objective module 70 into second beam path, i.e. 74A. Moving SLT module 40 and scanner module 60 into the optical path 13 of laser pulse of pulsed Nd:YAG laser 10 at first wavelength 1064 nm, enables: 1. frequency doubling to 532 nm by nonlinear crystals 41; 2. integration of the frequency doubled laser pulse with the SLT aiming beam within the energy meter/aiming beam module 20; 3. a detour around PD module 30 with lenses 31, 32 forming Galilean beam expander, by the means of two fixed mirrors 43, 44, and then via two beam shaping lenses 45, 46 forming SLT Galilean beam expander focusing on mirror 61 within the scanning module 60; alternatively this detour around PD beam expander can be achieved by using a photonic cable and two collimating lenses (not shown in FIG. 2). In SLT mode the switching mirror 61 is in switched on position and reflects the pulse from the SLT module 40 to a fixed mirror 62, a correction prism 63 and a pair of Risley prisms 64, 65 that enable scanning along x and y axis in the image plane 72A in the patient's eye 71. The correction prism 63 enables shifting the beam or pulse out of the singularity zone of the Risley prisms. Alternatively, scanning can be achieved without the correction and Risley prisms by replacing the fixed mirror 62 with a scanning mirror (not shown in FIG. 2).

PC mode (FIG. 3) is enabled by optomechanically coupling the 532 nm continuous wave (CW) laser module 15 with PC module 50, scanner module 60 and exit objective module 70 into third beam path, i.e. 74B. PC mode is enabled when electro-mechanically movable SLT/PC plat-form 80 composed of SLT module 40, PC module 50 and scanner module 60 is moved into the optical path 13 of laser pulse of PD module and the PD mode is switched out by shutter 23, while SLT mode is disabled by positioning the switchable mirror 61 out of SLT optical path into position 61A, thus enabling optical coupling of the CW laser beam from PC laser module 15 via a optical fiber 16 with PC module 50, scanner module 60 and exit objective module 70. When MLTD is operating in the PC mode, PD mode and SLT mode are disabled by closing the safety shutter 23 of the energy meter/aiming beam module 20 and switching mirror 61 of scanner module 60 to position 61A. Within module 60, a fixed mirror 62 reflects the beam on correction prism 63 and a pair of Risley prisms 64, 65 that enable scanning along x and y axis in the image plane 72B in the patient's eye 71. The correction prism 63 enables shifting the beam out of the singularity zone of the Risley prisms. Alternatively, scan-ning can be achieved without the correction and Risley prisms by replacing the fixed mirror 62 with a scanning mirror (not shown in FIG. 3).

Figure 4:
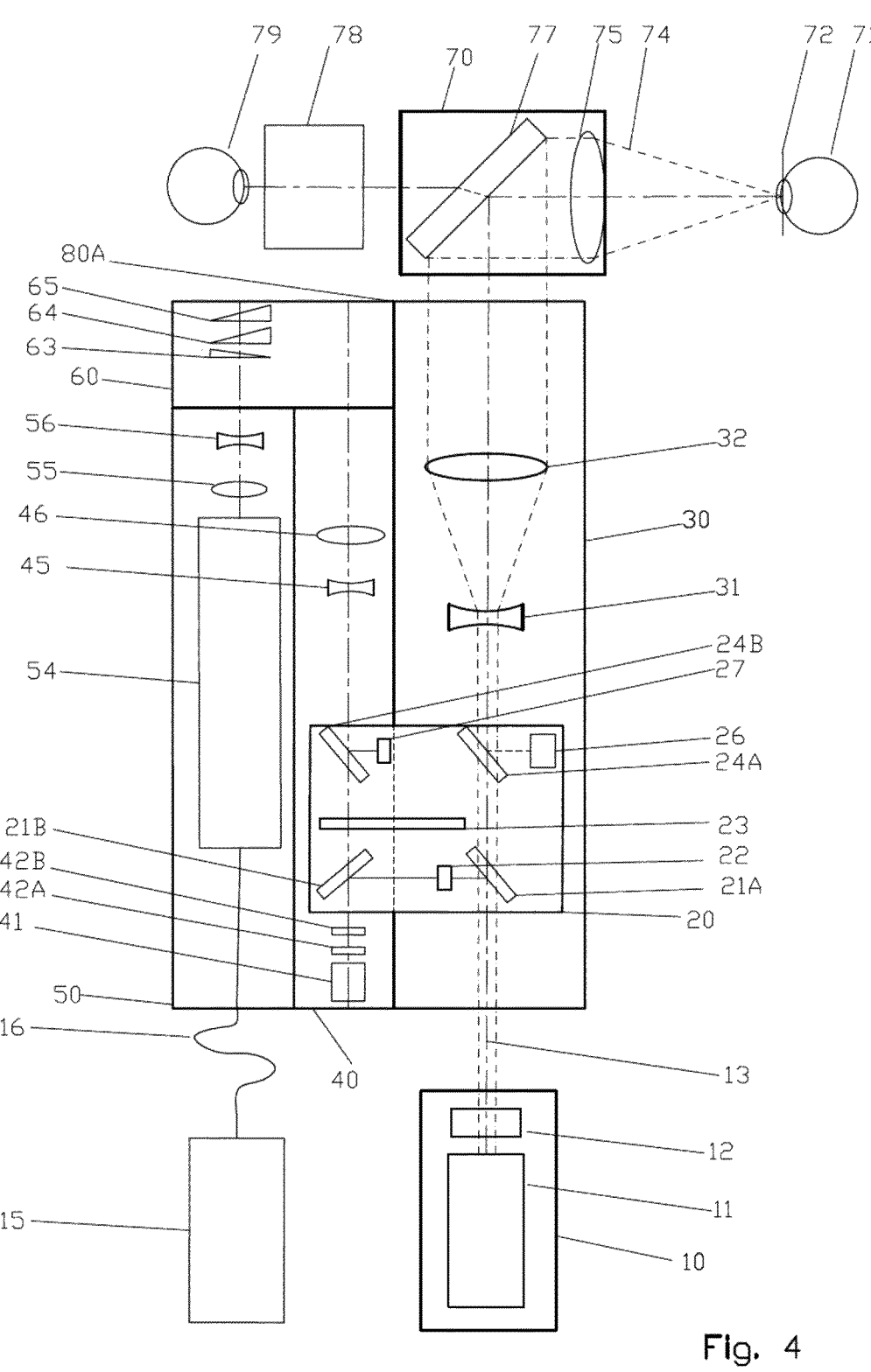
FIG. 4 shows an embodiment of a block diagram of the MLTD integrated on a single platform in a PD mode, in accordance with the invention.
Figure 5:
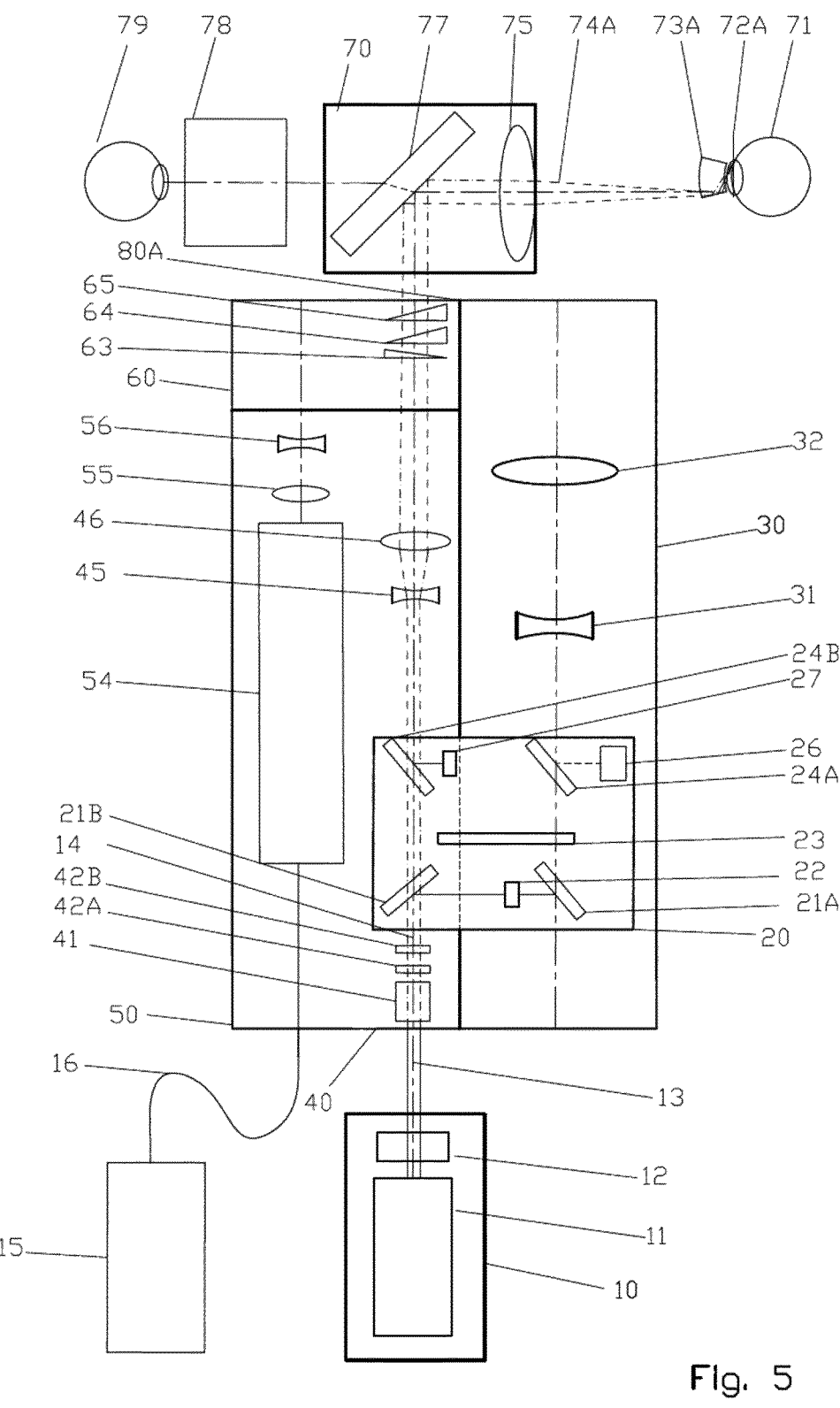
FIG. 5 shows an embodiment of a block diagram of the MLTD integrated on a single platform in a SLT mode, in accordance with the invention.

2) Optical Solution with One Platform (See FIG. 4, FIG. 5. And FIG. 6 for Details)

PD module 30, SLT module 40, PC module 50 are integrated on a single platform 80A that also includes the energy meter/aiming beam module 20 and scanning module 60. Within module 60, a correction prism 63 and a pair of Risley prisms 64, 65 that enable scanning along x and y axis in the image plane of the patient's eye 71 can have two discrete positions; one aligned with the optical path of module 40 when operating in the SLT mode and the second position aligned with optical path of module 50 when operating in PC mode. The correction prism 63 enables shifting the beam out of the singularity zone.

Switching between the desired mode of operation (PD, SLT or PC mode) is achieved by linear or rotational move-ment of the entire platform 80A to enable the coupling of the respective therapeutic laser source (either 10 or 15) with the appropriate optical module (30, 40 or 50 respectively) and with the same exit objective module 70 for image and waist formation in the eye of the patient 71.

PD mode (FIG. 4) is enabled by moving platform 80A in position in which the optical path 13 of laser pulse of the Nd-Yag pulsed laser module 10 at first wavelength 1064 nm is aligned with the energy meter/aiming beam module 20, PD module 30 with lenses 31 and 32 forming Galilean beam expander, and the exit objective module 70 into one optical path, i.e. first beam path 74.

SLT mode (FIG. 5) is enabled by moving platform 80A in position in which the optical path 13 of the Nd-Yag pulsed laser module 10 at first wavelength 1064 nm is colinear with the optical path of the SLT module 40 thus enabling: 1. frequency doubling to 532 nm by nonlinear crystals 41; 2. integration of the frequency doubled laser pulse with the SLT aiming beam within the energy meter/aiming beam module 20; 3. focusing of therapeutic and aiming beam via two beam shaping lenses 45, 46 forming SLT Galilean beam expander; 4. coupling with scanning module 60 by sliding the Correction prism 63 and a pair of Risley prisms 64, 65 in the optical path; and 5. coupling with the optical path of the exit objective module 70 into one optical path, i.e. second beam path 74A.

PC mode (FIG. 6) is enabled by moving platform 80A to position which enables optomechanically coupling the 532 nm CW laser beam from PC laser module 15 via fiber cable

16 with PC module 50, scanning module 60 and exit objective module 70 into one optical path, i.e. third beam path 74B.

When MLTD is operating in the PC mode, PD mode and SLT mode are disabled by closing the safety shutter 23 of the energy meter/aiming beam module 20.

DETAILED DESCRIPTION OF THE EMBODIMENTS

FIG. 1 depicts the Modular Laser Therapy Device (MLTD) operating in the photodisruptor (PD) mode.

The PD mode is enabled by integrating the Nd-Yag pulsed laser module 10, with energy meter/aiming beam module 20, the PD module 30 and the exit objective module 70 into one optical path, i.e. first beam path 74. When MLTD is oper-ating in the PD mode, SLT mode and PC mode are disabled by switching out SLT/PC platform 80 electromechanically from the PD optical path.

Nd-Yag pulsed laser module 10 consists of the Nd:YAG laser source 11 and variable attenuator 12. Nd-Yag pulsed laser is pumped by a flash or diode that emits short laser pulses of 1-5 ns and emitting energies from 0.3 to 10 mJ in the infrared region at a wavelength 1064 nm with a constant orientation of polarization. This short linearly polarized pulse exits laser module 10 through the attenuator 12 that enables regulation of the output energy by means of a coupled polarization rotator and a fixed polarizer. The attenuator 12 consists of plate $\lambda/2$ and polarizing filter. The position of rotation of the plate $\lambda/2$ can be set electrome-chanically to regulate how much of the input pulse will be transmitted through polarizer, which enables energy setting of the PD.

The pulsed laser beam with wavelength 1064 nm then passes through the energy meter/aiming beam module 20, consisting of beam splitter mirror 21, energy meter 22, safety shutter 23, beam combiner 24, polarizing beam split-ter/combiner 25 and two distinct aiming beam generators: aiming beam PD emitter 26 with double aperture 26A and aiming beam SLT emitter 27. When the short laser pulse exits the Nd-Yag pulsed laser module 10 and enters the energy meter/aiming beam module 20, the beam splitter 21 first reflects a small portion of the pulse towards the energy meter 22, while the major part of the pulse passes the safety shutter 23 and exits module 20 through the beam combiner 24. Positioning of the safety shutter 23 after the energy meter allows automatic closure of the shutter if energy meter detected higher energy pulses when MLTD is operating in PD mode and also if energy meter detected any light when PD mode is switched off. The beam combiner 24 allows collinear reflection of the PD aiming beam with wavelength 635 to 650 nm into the optical path of the therapeutic laser pulse with wavelength 1064 nm. The PD aiming beam is generated by the aiming beam PD emitter 26 that uses a diode that emits collimated S polarized beam with wave-length 635 to 680 nm which is then transmitted through double aperture 26A thus generating two aiming beams for PD mode that are then reflected from polarizing beam splitter/combiner 25 with high reflectivity for S polarization to beam combiner 24 which has high reflectivity for 635 nm in S and P polarization. Beam combiner 24 collinearly projects the therapeutic beam and the two PD aiming beams to the PD module 30 with lenses 31, 32 forming Galilean beam expander where the two aiming beams are magnified, then they are reflected from dichroic mirror 77 and focused to a single 20-40 µm spot in focal plane 72 of the patient's eye 71. Any deviation from focal plane is shown as defocused double spot, instead of single spot. Such double PD aiming beam allows precise focusing in PD mode.

Within the PD module 30 therapeutic and both aiming beams are expanded by first passing through Galilean beam expander composed of a negative lens 31 which diverges the laser pulse and the PD aiming beams and a positive lens 32 which collimates the 1064 nm pulse and the PD aiming beams to afocal mode.

Within the exit objective module 70, the 1064 nm pulse and the PD aiming beam are then reflected by a dichroic mirror 77 and focused by means of exit objective lens 75 in laser focus 72 in the patient's eye 71 where optical breakdown is achieved. The dichroic mirror 77 reflects the PD mode wavelength (nominally 1064 nm) or SLT mode wavelength (nominally 532 nm) of the laser pulse and also transmits the visible wavelengths of the light from the slit lamp being back-reflected or scattered from the patient's eye thus enabling the ophthalmologist 79 to monitor the patient's eye 71 through the binocular 78. The aiming beam enables the ophthalmologist 79 to monitor via binocular 78 where the optical breakdown will appear in the patient's eye 71.

Optical breakdown achieved in PD mode is used for capsule surgery in order to remove secondary cataract, for vitrectomy to remove the symptomatic floaters or for iridotomy.

FIG. 2 depicts the Modular Laser Therapy Device (MLTD) operating in the selective laser trabeculoplasty (SLT) mode.

The SLT mode is enabled by optomechanically coupling electromechanically movable SLT/PC platform 80 so that the SLT module 40 is inserted into the optical path 13 of the laser pulse exiting from the Nd-Yag pulsed laser module 10, first allowing frequency doubling of the pulse, then transmitting the 532 nm laser pulse through the energy meter/aiming beam module 20, and using two fixed mirrors 43, 44 for diverting the optical path around PD module 30 with lenses 31, 32 forming Galilean beam expander, and then transmitting the pulse via two beam shaping lenses 45, 46 forming SLT Galilean beam expander, to mirror 61 switched to SLT mode, and via scanning module 60 to the exit objective module 70 integrated in the second beam path, i.e. 74A. Electromechanically movable SLT/PC platform 80 is moved into the optical path 13 of laser pulse emitted out of the Nd-Yag pulsed laser module 10 using linear or rotational movement.

Instead of diverting the SLT laser pulse around the Galilean beam expander lenses 31, 32 in PD module 30, by reflecting it with two fold mirrors 45, 46, the laser pulse can be transmitted via optical photonic cable (not shown in FIG. 2). Photonic core glass fiber with a silver reflective coating enables convenient delivery of high energy pulsed lasers. Coupling efficiency can be near 100% and pulse dispersion is negligible. Such fibers have been used to deliver 50 mJ/5 ns pulse laser beams with wavelengths at 532 nm over a 5 m length. The invention can use short version of hollow photonic fiber with typical hollow core diameter of 300, 500, 700 or 1000 μm. The output of hollow core is imaged with exit collimating lens to exit objective lens 75, forming relay optical system producing magnification close to −0.8× for 500 μm diameter hollow fiber to produce an image with diameter 400 μm in focal plane 72A. Optical photonic cable with an entry focusing and an exit collimating lens simplifies the optical path within the SLT module by replacing fold mirror 44 and SLT Galilean beam expander lenses 45, 46 and collimating the laser pulse back to mirror 61 (not shown in FIG. 2).

The laser pulse for SLT mode is generated and regulated by the Nd-Yag pulsed laser module 10 as described in detail under FIG. 1. The pulsed beam then passes through the first part of the electromechanically movable SLT/PC module 40 containing KTP crystal 41 and pass filter 42A and attenuator 42B. The laser pulse with initial wavelength 1064 nm is frequency doubled by the transmission through the non-linear crystal 41 to a wavelength of 532 nm. The optical system makes use of the frequency doubling module comprised of one or two non-linear crystals 41. The advantage of using one non-linear crystal is preservation of linear output polarization, however doubling stability is poorer than in configuration with two non-linear crystals. On the other hand, the advantage of using two non-linear crystals is better energy stability of frequency doubling, whereas a drawback is undefined output polarization. The remainder of the wavelength of 1064 nm that was not converted in the non-linear crystal 41 gets absorbed in the pass filter 42A. Bandpass filter 42A transmits the wavelength of 532 nm and absorbs the wavelength of 1064 nm thus allowing operation without a presence of disturbing wavelengths. SLT attenuator 42B allows for the adjustment of SLT energy output.

The frequency doubled pulse then passes through the energy meter/aiming beam module 20. Within this module 20, the beam splitter 21 first reflects a small portion of the 532 nm pulse towards the energy meter 22, while the major part of the pulse passes the safety shutter 23 and exits module 20 through the beam combiner 24. The beam combiner 24 is dichroic mirror that allows collinear reflection of the aiming beam with wavelength 635 to 650 nm into the optical path of the therapeutic SLT laser pulse with wavelength 532 nm. The aiming beam is generated by the aiming beam SLT emitter 27 and is transmitted by polarizing beam splitter/combiner 25 on the beam combiner 24 that collinearly transmits the therapeutic 532 nm pulse and reflects the aiming beam on the SLT module, first on two fixed mirrors 43, 44, and then via two beam shaping lenses 45, 46 forming SLT Galilean beam expander transmitting to a switchable mirror 61, then to fixed mirror 62, a correction prism 63 and a pair of Risley prisms 64, 65 that enable scanning along x and y axis in the image plane 72A in the patient's eye 71. A correction prism 63 is incorporated to avoid both the singularity blindspot of the Risley prism pair 64, 65. Correction prism 63 thus provides an additional degree of freedom to the Risley prism pair 64, 65 and shifts the singularity off-axis. Continuous orientation of correction prism 63 allows tracking a target through the singularity so that the Risley control equations no longer have two, but an infinite number of solutions for the same elevation and azimuth target angles. Risley prisms 64, 65 are shown in maximum derivation position where the pulse is maximally deviated from optical path, i.e. second beam path 74A.

Alternatively, scanning can be achieved without the correction and Risley prisms by replacing the fixed mirror 62 with a scanning mirror (not shown in FIG. 2).

Within the exit objective module 70 the laser pulse is reflected by the dichroic mirror 77 and is focused by means of the exit objective lens 75 and an add-on lens 73A in the focal plane 72A in the patient's eye 71. The dichroic mirror 77 reflects the PD mode wavelength (nominally 1064 nm) or the SLT mode wavelength (nominally 532 nm) of the laser pulse and also transmits the aiming beam and the visible wavelengths of the light from the slit lamp being back-reflected or scattered from the patient's eye thus enabling the ophthalmologist 79 to monitor the patient's eye 71 through the binocular 78.

PC mode is disabled by internal safety shutter of the laser source 15 and by switchable mirror 61 blocking beam from PC zoom optics 54.

Figure 3:
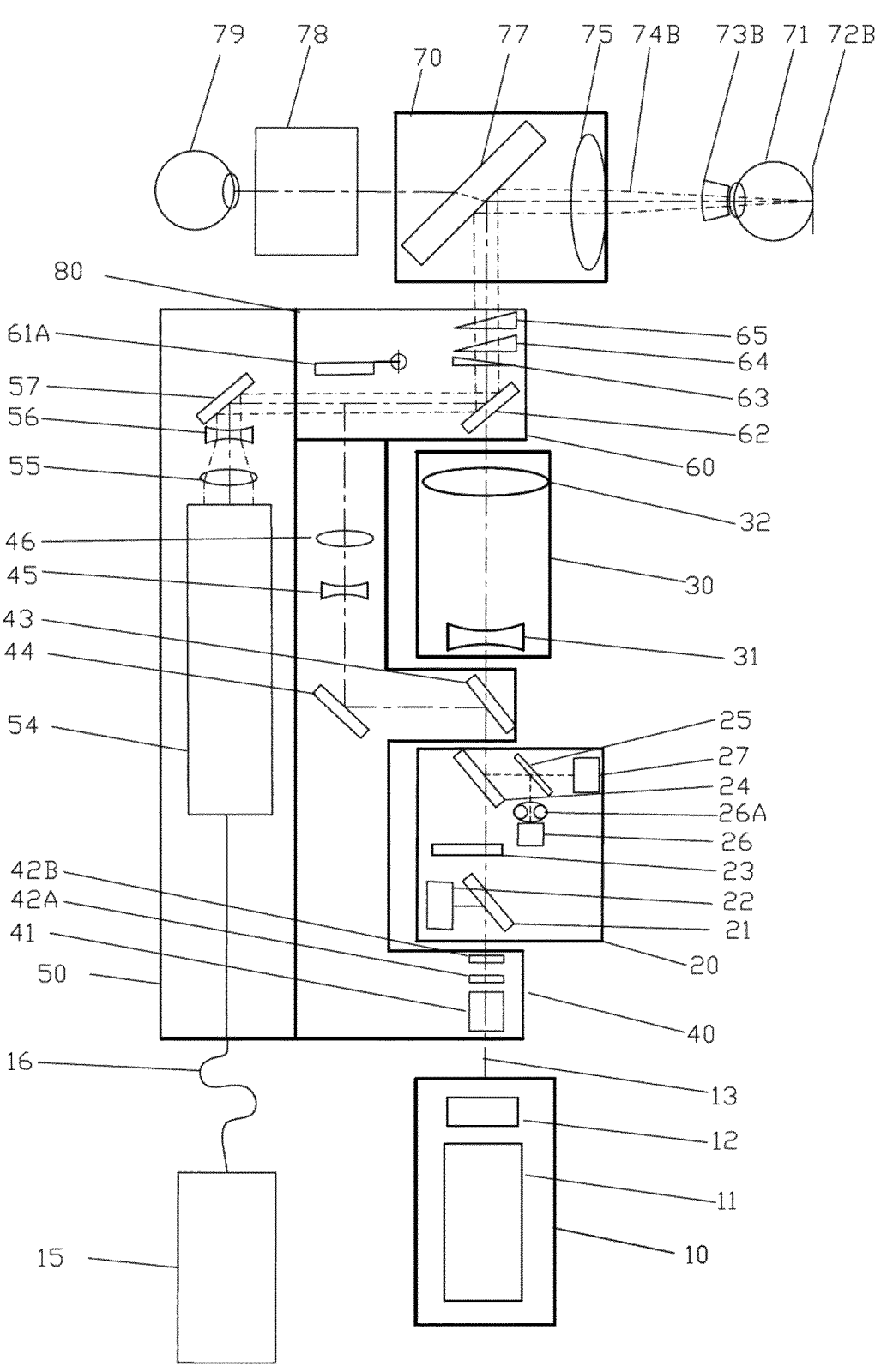
FIG. 3 shows an embodiment of a block diagram of the MLTD consisting of two platforms in a Photocoagulator (PC) mode, in accordance with the invention.

FIG. 3 depicts the Modular Laser Therapy Device (MLTD) operating in the photocoagulator (PC) mode.

The PC mode is enabled by optomechanically coupling the 532 nm continuous wave PC laser module 15 with PC module 50, scanner module 60 and exit objective module 70 by positioning SLT/PC platform 80 in optical path 13 of laser pulse of the PD module 30. SLT/PC platform 80 is composed of SLT module 40, PC module 50 and scanner module 60. PC module 50 contains delivery laser beam optical fiber 16, zoom optical system 54 and exit optics composed of beam shaping lenses 55, 56 forming a PC Galilean beam expander/compressor and mirror 57. When MLTD is operating in the PC mode, PD mode is disabled by positioning SLT/PC platform 80 in optical path of the PD module 30, while SLT mode is disabled by positioning switchable mirror 61 out of the optical path of the SLT laser beam into position 61A. In addition, when MLTD is operating in the PC mode, PD mode and SLT mode are disabled by closing the safety shutter 23 of the energy meter/aiming beam module 20. Switching between the three different modes of MLTD (PD, SLT and PC) is achieved by electro-mechanical, electronic and microprocessor control.

The 532 nm CW PC laser module 15 consists of a 532 nm CW PC laser source with the internal power meter, safety shutter, aiming beam PC emitter, beam combiner and fiber collimating lens that collimates the PC beam and the aiming beam to optical fiber 16 and a zoom optical system 54 of the PC module 50.

Depending on the particular ophthalmic treatment mode, different PC laser sources 15 that emit 532 nm continuous wave laser beam may be used, such as: CW frequency-doubled Nd:YAG laser with a wavelength of 532 nm; diode-pumped solid state laser with a wavelength of 532 nm, power 50 mW to 2.5 W and exposure time of 0.001 s to 3 s; or diode-pumped solid state laser with a wavelength of 577 nm, power 50 mW to 2.5 W and exposure time of 10 us to 5 s.

A small portion of the 532 nm or 577 nm continuous wave laser beam emitted from the laser source 15 is reflected by the internal beam splitter towards the internal power meter, while the major part of the beam passes the internal safety shutter and is transmitted through internal beam combiner to the fiber collimating lens. Whenever the internal power meter detects an unsafe condition, the internal safety shutter blocks the third beam path before the therapeutic laser beam exits the laser module 15 and thus prevents damage to the eye of the patient. The beam combiner allows collinear reflection of the aiming beam with wavelength 635 nm to 650 nm into the optical path of the therapeutic PC laser beam with wavelength 532 nm. The aiming beam is generated by the internal aiming laser beam PC emitter. The aiming laser beam PC emitter may suitably produce the desired aiming beam as a CW having a wavelength in the range of 635 nm to 650 nm, with a lower power density as compared to the treatment laser beam from laser source 15, for example a solid-state diode laser which provides a 635 nm red beam can be used. The aiming beam may have an average continuous wave output power of no more than 1 mW.

The aiming beam is reflected by the internal beam combiner to the fiber collimating lens collinearly with the therapeutic PC laser beam, so the therapeutic and the aiming beam are transmitted collinearly via the optical fiber 16 and transmitted to the zoom optical system 54. The size of the relevant laser beam is largely determined by the core diam-eter and the numerical aperture (NA) of the laser beam delivery fiber 16. A typical delivery fiber for ophthalmic laser systems has a 50 μm diameter core with a 0.12 NA. With fiber diameter 50 μm, image spot diameter is usually from 50 to 1000 μm at magnification 1 to 20×. The smallest spot size desired by the ophthalmic treatment laser market is 50 μm, but the necessary NA of the laser delivery system is between 0.06 and 0.09.

The optical fiber with usual diameter of core 50 microm-eters and NA 0.12 functions as beam homogenizer, so at the exit the fiber is emitting tophat profile laser beam to a zoom optical system 54, which magnifies beam size by 1 to 20 times.

Instead of a laser source generating CW at 532 nm and fiber coupling with zoom optics 54, a CW laser diode with wavelengths from 440 to 680 nm can be integrated into module 50 and directly coupled to zoom optics 54, without using fiber 16. Such configuration is even more compact and has no external fiber cable which can be damaged (not shown in FIG. 3)

Zoom optical system 54 transmits afocal beam to beam shaping lenses 55, 56 forming a small PC Galilean beam expander/compressor for adjusting the beam and spot size and is then reflected from mirror 57 to the scanning module 60. With the switching mirror 61 moved out of the optical path to position 61A the CW beam is then reflected by fixed mirror 62, and via a correction prism 63 and a pair of Risley prisms 64, 65 to the exit objective lens module 70. Alter-natively, fixed mirror 62, correction prism 63 and Risley prisms 64, 65 can be replaced by a scanning mirror to enable scanning along x and y axis in the image plane 72B on the retina of the patient's eye 71 (not shown in FIG. 3). In PC mode a CW laser beam is directed to the patient's eye along an optical path, i.e. third beam path 74B.

Within the exit objective module 70 the CW beam is reflected by dichroic mirror 77 and is focused by means of the exit objective lens 75 and an add-on lens 73B in the focal plane 72B in the patient's eye 71. The dichroic mirror 77 reflects the PD mode wavelength (nominally 1064 nm) or the SLT mode wavelength (nominally 532 nm) of the laser pulse and also transmits the wavelengths of the aiming beam and the light from the slit lamp being back-reflected or scattered from the patient's eye thus enabling the ophthal-mologist 79 to monitor the patient's eye 71 through the binocular 78.

FIG. 4 depicts the device integrated on a single platform operating in a photodisruptor (PD) mode.

PD mode is enabled by moving platform 80A in position in which the optical path 13 of laser pulse of the Nd-Yag pulsed laser module 10 at first wavelength 1064 nm is aligned with the energy meter/aiming beam module 20, PD module 30 with lenses 31, 32 forming PD Galilean beam expander, and the exit objective module 70 into one optical path, i.e. first beam path 74.

When MLTD is operating in the PD mode, SLT mode is disabled as it is not colinear with the laser source module 10, while PC mode is disabled by shutting off the PC laser module 15.

Nd-Yag pulsed laser module 10 consisting of the Nd:YAG laser source 11 and variable attenuator 12 is described in detail under FIG. 1.

The emitted short laser pulse of 1-5 ns with energies from 0.3 to 10 mJ in the infrared region at a wavelength 1064 nm and with a constant orientation of polarization passes through the energy meter/aiming beam module 20, consist-ing of beam splitter mirror 21A, energy meter 22, safety shutter 23, beam combiner 24A and two distinct aiming beam generators: aiming beam PD emitter 26, double aperture 26A and aiming beam SLT emitter 27. When the short laser pulse with a wavelength 1064 nm exits the Nd-Yag pulsed laser module 10 and enters the energy meter/aiming beam module 20, the beam splitter 21A first reflects a small portion of the pulse towards the energy meter 22, while the major part of the pulse passes the safety shutter 23 and exits module 20 through the beam combiner 24A. Positioning of the safety shutter 23 after the energy meter allows automatic closure of the shutter if energy meter detected higher energy levels when MLTD is operating in PD mode and also if energy meter detected any light when PD mode is switched off. The beam combiner 24A allows collinear reflection of the PD aiming beam with wavelength 635 to 650 nm into the optical path of the therapeutic laser pulse with wavelength 1064 nm.

The PD aiming beam is generated by the aiming beam PD emitter 26 that uses a diode emitting collimated beam with wavelength 635 to 680 nm which is then transmitted through double aperture 26A thus generating two aiming beams for PD mode that are then reflected to beam combiner 24A that collinearly transmits the therapeutic beam or pulse and the PD aiming beam to PD module 30 where both aiming PD beams are magnified by Galilean beam expander lenses 31,32, reflected from dichroic mirror 77 and focused to a single 20-40 μm spot in focal plane 72. Any deviation from focal plane is shown as defocused double spot, instead of single spot. Such double PD aiming beam allows precise focusing in PD mode.

Within the PD module 30 the therapeutic 1064 nm pulse and both aiming beams pass the Galilean beam expander; first passing through a negative lens 31 which diverges the laser pulse and the PD aiming beams and then through a positive lens 32 which collimates the 1064 nm pulse and the PD aiming beams to afocal mode.

Within the exit objective module 70, the 1064 nm pulse and the PD aiming beam are then reflected by a dichroic mirror 77 and focused by means of exit objective lens 75 in laser focus 72 in the patient's eye 71 where optical breakdown is achieved. The dichroic mirror 77 reflects the PD mode wavelength (nominally 1064 nm) or SLT mode wavelength (nominally 532 nm) of the laser pulse and also transmits the wavelengths of the aiming beam and the light from the slit lamp being back-reflected or scattered from the patient's eye thus enabling the ophthalmologist 79 to monitor the patient's eye 71 through the binocular 78. The aiming beam enables the ophthalmologist 79 to monitor via binocular 78 where the optical breakdown will appear in the patient's eye 71.

Optical breakdown achieved in PD mode is used for capsule surgery in order to remove secondary cataract or for iridotomy.

FIG. 5 depicts the device integrated on a single platform operating in the selective laser trabeculoplasty (SLT) mode.

SLT mode is enabled by linearly moving or rotating platform 80A to position in which the optical path 13 of laser pulse of the Nd-Yag pulsed laser module 10 at first wavelength 1064 nm is colinear with the optical path of the SLT module 40 thus enabling: 1. frequency doubling to 532 nm by nonlinear crystals 41, 2. integration of the frequency doubled laser pulse with the SLT aiming beam within the energy meter/aiming beam module 20; 3. focusing of therapeutic and aiming beam via two beam shaping lenses 45, 46 forming SLT Galilean beam expander; 4. coupling with scanning module 60 by moving the correction prism 63 and a pair of Risley prisms 64, 65 in the optical path; and 5.

coupling with the optical path of the exit objective module 70, the second beam path, i.e. 74A.

The laser pulse for SLT mode is generated and regulated by the Nd-Yag pulsed laser module 10 as described in detail under FIG. 1. The laser pulse with initial wavelength 1064 nm is frequency doubled to a third wavelength of 532 nm in the SLT module 40 by the transmission through the non-linear crystal 41 as described in more detail under FIG. 2. The remainder of the wavelength of 1064 nm that was not converted in the non-linear crystal 41 gets absorbed in the pass filter 42A thus allowing operation without a presence of disturbing wavelengths, while SLT attenuator 42B allows for the adjustment of SLT energy output.

The frequency doubled pulse with the wavelength 532 nm then passes through the energy meter/aiming beam module 20. Within this module 20, the beam splitter 21B first reflects a small portion of the 532 nm pulse towards the energy meter 22, while the major part of the pulse passes the safety shutter 23 and exits module 20 through the beam combiner 24B. The beam combiner 24B is dichroic mirror that allows collinear reflection of the aiming beam with wavelength 635 nm to 680 nm into the optical path of the therapeutic SLT laser pulse with wavelength 532 nm. The aiming beam is generated by the aiming beam SLT emitter 27 that uses a diode that emits collimated beam with wavelength 635 to 650 nm thus generating a single aiming beam for SLT mode that is then forming 0.4 mm spot in focal plane 72A of the patient's eye 71.

Beam combiner 24B collinearly transmits the therapeutic 532 nm pulse and reflects the aiming beam via two beam shaping lenses 45, 46 forming SLT Galilean beam expander directly on correction prism 63 and a pair of Risley prisms 64, 65 that enable scanning along x and y axis in the image plane 72A in the patient's eye 71. The correction prism 63 enables shifting the beam out of the singularity zone of the Risley prisms.

Within the exit objective module 70 the laser pulse is reflected by the dichroic mirror 77 and is focused by means of the exit objective lens 75 and an add-on lens 73A in the focal plane 72A in the patient's eye 71. The dichroic mirror 77 reflects the PD mode wavelength (nominally 1064 nm) or SLT mode wavelength (nominally 532 nm) of the laser pulse and also transmits the wavelengths of the aiming beam and the light from the slit lamp being back-reflected or scattered from the patient's eye thus enabling the ophthalmologist 79 to monitor the patient's eye 71 through the binocular 78.

PC mode is disabled by switching off the laser source 15, while PD mode is disabled by being positioned out of the optical path of the laser source module 10.

Figure 6:
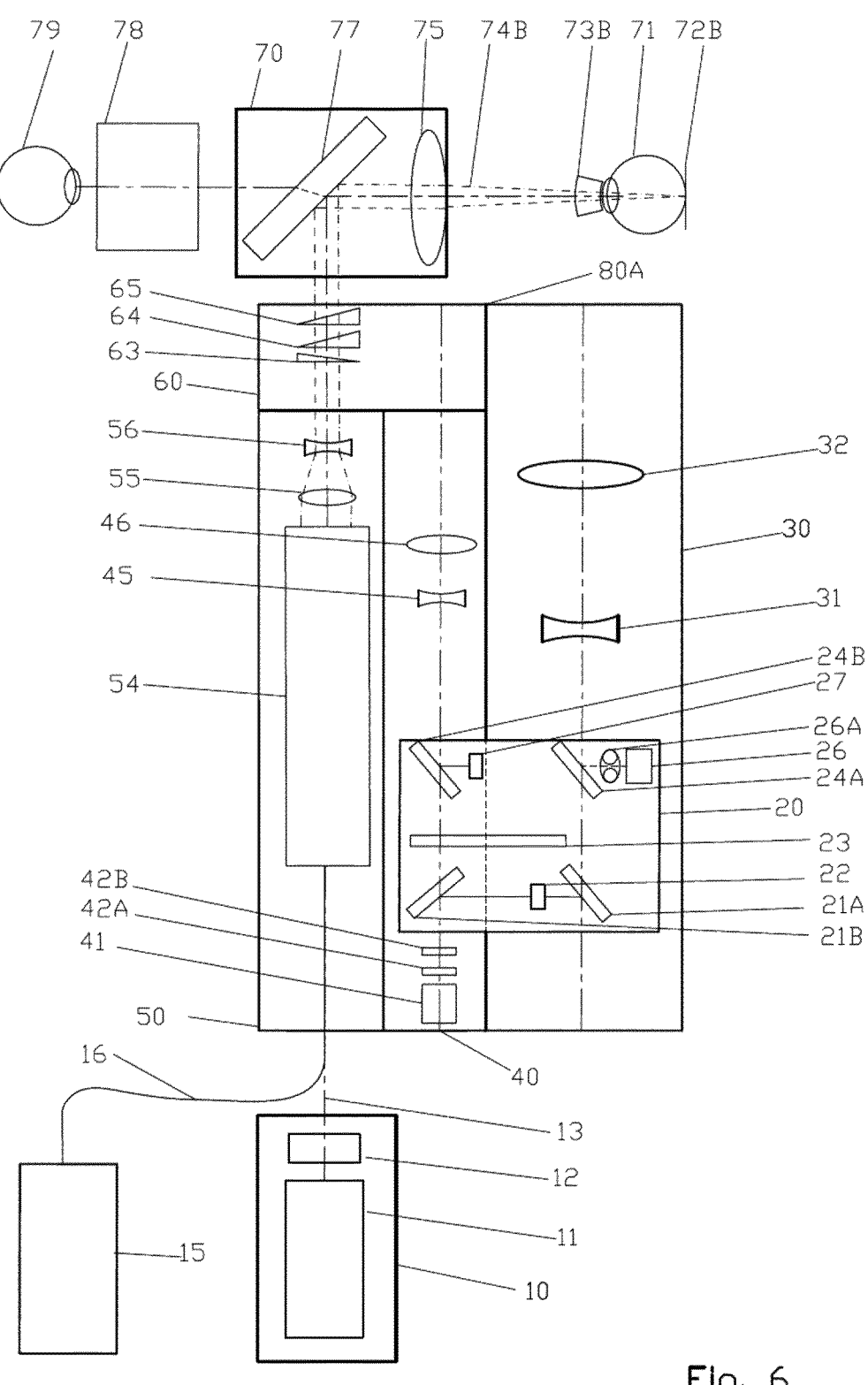
FIG. 6 shows an embodiment of a block diagram of the MLTD integrated on a single platform in a PC mode, in accordance with the invention.

FIG. 6 depicts the device integrated on a single platform operating in photocoagulator (PC) mode.

PC mode is enabled by moving platform 80A containing all three core optical modules to position which enables optomechanically coupling the 532 nm CW laser beam from PC laser module 15 via fiber cable 16 with PC module 50 that is colinear with scanning module 60 and exit objective module 70, enabling third beam path 74B. When MLTD is operating in the PC mode, PD mode and SLT mode are disabled by switching off the laser source in module 10 or by closing the safety shutter 23 of the energy meter/aiming beam module 20.

The 532 nm continuous wave PC laser module 15 is composed of a 532 nm CW PC laser source with the internal power meter, safety shutter, aiming beam PC emitter, beam combiner and fiber collimating lens that collimates the PC beam and the aiming beam via optical fiber 16 with a zoom optical system 54 of the PC module 50.

Instead of a laser source generating CW at 532 nm and fiber coupling with zoom optics 54, a CW laser diode with wavelengths from 440 to 680 nm can be integrated into module 50 and directly coupled to zoom optics 54, without using fiber 16. Such configuration is even more compact and has no external fiber cable which can be damaged (not shown in FIG. 6).

The properties of the PC laser source 15 and the emitted 532 nm continuous wave laser beam, the generation and properties of the aiming beam and the properties of the delivery optical fiber are explained in more detail under description of FIG. 3.

The therapeutic and the aiming beam are transmitted collinearly via the optical fiber 16 to the zoom optical system 54 of PC module 50. Zoom optical system 54 transmits afocal beam to the beam shaping lenses 55, 56 forming a small PC Galilean beam expander/compressor for adjusting the beam and spot size projected to the scanning module 60 that is colinear with the exit objective module 70. Within module 60, a correction prism 63 and a pair of Risley prisms 64, 65 that enable scanning along x and y axis in the image plane 72B of the patient's eye 71 are aligned with optical path of module 50 when operating in PC mode. The fixed correction prism 63 enables shifting the beam out of the singularity zone of the Risley prisms.

Within the exit objective module 70 the CW beam is reflected by dichroic mirror 77 and is focused by means of the exit objective lens 75 and an add-on lens 73B in the focal plane 72B in the patient's eye 71. The dichroic mirror 77 reflects the PD mode wavelength (nominally 1064 nm) or SLT mode wavelength (nominally 532 nm) of the laser pulse and also transmits the wavelengths of the aiming beam and the light from the slit lamp being back-reflected or scattered from the patient's eye thus enabling the ophthalmologist 79 to monitor the patient's eye 71 through the binocular 78.

The invention claimed is:

1. An ophthalmic laser system comprising:
a first laser module operable to produce a first beam at a first wavelength;
a second laser module operable to produce a second beam at a second wavelength;
a first beam path incorporating an exit objective module, the first beam path directing the first beam to an eye of a patient;
a second beam path incorporating a non-linear crystal and the exit objective module, wherein the non-linear crystal converts the first beam or the second beam to a third beam at a third wavelength, the second beam path directing the third beam to the eye of the patient; and
a third beam path incorporating the exit objective module, the third beam path directing the second beam to the eye of the patient,
wherein the beam directed to the eyes of the patient is generated by either the first laser module or the second laser module.

2. The ophthalmic laser system of claim 1, wherein the first beam path, the second beam path, and the third beam path are configured for treatment of the eye of the patient.

3. The ophthalmic laser system of claim 1, wherein at least one of the first beam path, and/or the second beam path, and/or the third beam path, further incorporates beam shaping optics.

4. The ophthalmic laser system of claim 1, wherein the third wavelength is one-half the first wavelength.

5. The ophthalmic laser system of claim 1, wherein one laser module comprises a laser of a first type, and the other laser module comprises a laser of a second type different from the first type.

6. The ophthalmic laser system of claim 5, wherein the laser of the first type comprises a pulsed laser source and/or the laser of the second type comprises a continuous wave laser source.

7. The ophthalmic laser system of claim 1, wherein:
the first laser module comprises a pulsed Nd-YAG laser, the first wavelength being 1064 nm and suitable for secondary cataract treatment, the first wavelength when converted to the third wavelength being 532 nm and suitable for glaucoma treatment; and/or
the second laser module comprises a continuous wave laser or a laser diode, the second wavelength being from 440 nm to 650 nm, which is suitable for treatment with photocoagulation.

8. The ophthalmic laser system of claim 1, wherein:
the first beam path and/or the second beam path further incorporate a first safety module for blocking off the first beam path and/or the second beam path whenever the first safety module detects an unsafe condition; and/or
the third beam path incorporates a second safety module integrated within the second laser module, for blocking off the third beam path whenever an internal power meter of the second laser module detects an unsafe condition.

9. The ophthalmic laser system of claim 1, wherein the second beam path and/or the third beam path further incorporate a scanning module comprising a plurality of prisms and/or one or more mirrors.

10. The ophthalmic laser system of claim 1, comprising:
adaptable optomechanical coupling for at least part of all components and modules; and
electromechanical control, electronic control, and/or microprocessor control for selectively operating for and amongst the first beam path, the second beam path, or the third beam path.

11. The ophthalmic laser system of claim 1, wherein:
one of the laser modules is movably mounted; and/or
one of the laser modules is provided with a fiber coupling for selectively operating for and amongst the first beam path, the second beam path, or the third beam path.

12. The ophthalmic laser system of claim 11, wherein the first laser module is movably mounted and/or the second laser module is provided with the fiber coupling.

13. The ophthalmic laser system of claim 1, wherein:
components and modules for operating the first beam path are mounted on a first platform including the first laser module; and
components and modules for operating the second beam path are mounted on a second platform,
wherein at least one of the first platform and/or the second platform is movably mounted for selectively operating, by activating a linear and/or rotational movement of the at least one platform, either (a) components and modules including the first laser module or the first platform for operating the first beam path, or (b) components and modules of the second platform for operating the second beam path.

14. The ophthalmic laser system of claim 13, wherein:
components and modules for operating the third beam path are mounted on the second platform, and
the second laser module comprises a fiber coupling for selectively operating the third beam path.

15. The ophthalmic laser system of claim 13, wherein at least one movably mounted platform is operable to perform linear and rotational movements.

16. The ophthalmic laser system of claim 13, further comprising one or more mirrors for selectively deflecting the third beam toward beam shaping optics of the second beam path.

17. A method for use of the ophthalmic laser system of claim 1, the method comprising:

selectively switching the ophthalmic laser system among three different therapeutic modes of operation depending on a required ophthalmic laser treatment, the three different therapeutic modes of operation comprising:

(i) a photodisruptor mode wherein the first beam path is operable using the first laser module at the first wavelength;

(ii) a selective laser trabeculoplasty mode wherein the second beam path is operable using the first laser module at the third wavelength; and (iii) a photocoagulator mode wherein the third beam path is operable using the second laser module at the second wavelength.

18. The method of claim 17, wherein:

the selectively switching is enabled by adaptable optomechanical coupling for at least part of all components and modules of the beam paths, and by electromechanical, electronic, and/or microprocessor control; and/or either at least one of the laser modules is movably mounted, or part of all components and modules of the beam paths is mounted onto a movable platform.

\* \* \* \* \*